United States Patent

Henry et al.

[11] Patent Number: 5,904,721
[45] Date of Patent: May 18, 1999

[54] PROSTHETIC COMPONENT WITH PNEUMATIC DEVICE FOR KNEE ARTICULATION

[75] Inventors: Philippe Henry, Montgeron; Jean-Yves Audran, Sucy-En-Brie, both of France

[73] Assignee: Proteval, Valenton, France

[21] Appl. No.: 08/659,592

[22] Filed: Jun. 6, 1996

[30] Foreign Application Priority Data

Jun. 9, 1995 [FR] France ................................. 95 06875

[51] Int. Cl.⁶ ................................. A61F 2/64; A61F 2/74
[52] U.S. Cl. ................................. 623/26; 623/44
[58] Field of Search ................................. 623/43, 44, 46, 623/45, 39–42, 26; 601/5, 33

[56] References Cited

U.S. PATENT DOCUMENTS 3,474,466 10/1969 Collins ................................. 601/40 X

FOREIGN PATENT DOCUMENTS

| 952455 | 11/1949 | France . | |
| 9405545 | 6/1994 | Germany . | |
| 1491508 | 7/1989 | U.S.S.R. | 601/33 |
| 982527 | 2/1965 | United Kingdom | 623/39 |
| 92 22267 | 12/1992 | WIPO . | |

*Primary Examiner*—David H. Willse
*Attorney, Agent, or Firm*—William H. Holt

[57] ABSTRACT

A prosthetic component with a pneumatic device for knee articulation formed of an upper part adapted to support a socket element for a stump of a thigh, and a lower part intended to receive a tube extended by an ankle and foot. The two parts are connected to each other by an assembly of pivoted links forming a deformable prism. Movement of the two parts between two stable positions of complete extension and flexure, about the variable axis of rotation defined by these connections, is controlled by a pneumatic cylinder having an upper chamber and a lower chamber separated by a piston and communicating with each other by an air duct with adjustable flow. In each of the stable positions, the pressure of air in the chambers is greater than 1 bar and is preferably between 4 and 7 bar.

11 Claims, 5 Drawing Sheets

PROSTHETIC COMPONENT WITH PNEUMATIC DEVICE FOR KNEE ARTICULATION

BACKGROUND OF THE INVENTION

The invention relates to a prosthetic component with a pneumatic device for articulation of the knee.

Such a prosthetic component is an essential element of an artificial leg prosthesis called an "above the knee", that is to say which has a foot, an ankle, a lower part of the leg hereinafter called a "leg", a knee and a socket for receiving the stump of the thigh.

The patient can perform a balancing movement with this type of prosthesis. If this movement is controlled in an appropriate manner, the ability to walk in a relatively natural way can thus be restored.

A large number of means for controlling the relative movement of the upper part of the prosthetic device (supporting the socket) with respect to its lower part (connected to the leg) are known from the prior art.

The basic function which this prosthetic device must perform is that of damping and propelling, which is generally provided by the use of springs, hydraulic or pneumatic cylinders, or by any combination of these means.

The British patent application GB-A-2,252,503, published on Aug. 12, 1992, gives an example of use of a pneumatic cylinder for controlling the movement of a prosthesis. The opening of the valve of the cylinder of the prosthetic component is controlled by a micro-processor as a function of the speed of walking. The use of a computer for producing the control signals for the valve of the cylinder as a function of the signal coming from an angle transducer between the thigh and the leg permits a sophisticated control of movements. However, this knee prosthesis component is pivoted about a fixed axis of rotation and therefore possesses movement characteristics rather far from those of a human knee.

The international patent application WO 93/22,991 published on Nov. 25, 1993 describes a mechanical articulation reproducing the kinematics of the normal human knee. The movement of the lower part of the articulation is guided by studs moving in curved grooves in the upper part, in such a manner that the axis of rotation is variable and no longer fixed.

The same kinematics can be produced by interconnection links as is shown in the European patent application EP-A1-0,590,386 filed by the German company Otto Bock Orthopädische Industrie and published on Apr. 6, 1994.

The international patent application WO 92/22,267 published on Dec. 23, 1992 has already shown a simultaneous embodiment of the above principles: a variable axis of rotation obtained by a set of links and a pneumatic cylinder having a function of damping and propulsion. The control of the flexure and extension of the articulation being however produced differently by the flow of a fluid in a hydraulic cylinder controlled by an electro-magnetic valve.

The pneumatic prosthetic component for articulation of he knee sold by the Proteval company under the name "Acphapend" has the advantages of the first three prior devices but is an entirely mechanical and pneumatic product, which is consequently simpler and more reliable.

In certain conditions of use, particularly for running, a prosthesis having a hydraulic system is more suitable. The device described in the WO 92/22,267 specification can thus represent a good compromise. However, the mass of fluid renders the device significantly heavier than an entirely pneumatic apparatus, and thus tiring for its user.

The European patent application EP-A1-0,628,296 filed by the Chas. A. Blatchford & Sons company and published on Dec. 14, 1994 describes a control system for a prosthesis which uses the same principles as those described in the GB-A-2,252,503 specification. The patient is also provided with a electronic circuit for automatic control. It is clear that with the possibility of no longer having to make adjustments on the prosthetic component as such is a significant comforting factor for the patient; further, these adjustments can then be made during walking.

It is in taking account of all these constraints that the new prosthetic component for articulation of the knee according to the present invention has been conceived; an entirely mechanical and pneumatic product, similar to the product known under the "Acphapend" name, it also provides a little more closely the same characteristics, adjustable at will, as those of a hydraulic knee. Combining, on the one hand, the comfort of remote adjustment of the orthopaedic characteristics which are a feature of electronic systems and, on the other hand, the stiffness necessary in certain sporting activities exhibited only by hydraulic knees, whilst being lighter, more simple and more reliable than these latter, the invention offers advantages unknown at present in the state of the art.

GENERAL DESCRIPTION OF THE INVENTION

The present invention thus envisages relieving the inconveniences of the prosthetic components used in known knee prostheses.

More precisely its object is a pneumatic prosthetic component for articulation of the knee, known in part in itself from the state of the art in that it is formed from an upper part, adapted to support a socket element for the stump of the thigh, and of a lower part intended to receive a tube extended by a foot with an ankle. In an equally known manner, these two parts are connected to each other by an assembly of pivoted links forming a deformable prism; the relative movement of the said two parts between two stable positions of extension and complete flexure, about the variable axis of rotation defined by these connections, is controlled by a pneumatic cylinder; the upper chamber and the lower chamber delimited in the cylinder by a piston, communicate with each other via an adjustable flow air duct; the pneumatic cylinder has the usual function of damping at the end of the stroke and of propelling by compression of air for return from the flexure position to the extension position.

The prosthetic component the object of the present invention is characterised in that, in each of the said stable positions, the pressure of air in the said chambers is above 1 bar and is preferably between 4 and 7 bar.

In accordance with a preferred embodiment, the air duct connecting the two chambers is advantageously in communication with the outside air via a first non-return valve for inflation via which said air duct 32, 33 is in communication with the ambient air.

According to another preferred embodiment, the first arm of the air duct connecting the first non-return valve to the upper chamber has another non-return valve and a first valve in parallel. The second arm of the said air duct connecting the first inflation valve to the lower chamber also has the same devices, that is to say a third non-return valve and a second valve in parallel.

According to another feature of the invention, the two arms of the air duct are constituted by flexible tubes of sufficient length for permitting the control of each of these two valves from the socket or the waist which improves the comfort of use. With the same objective, the control of the valves preferably has several pre-defined settings, preferably two. This can be brought about thanks to valves constituted by an obturator with several positions, preferably two.

In a first variant of the apparatus according to the invention the pressure required in the said chambers can be obtained by compressing ambient air with an associated inflation device.

According to another variant of the apparatus according to the invention, thanks to a set of valves and non-return valves, the ambient air is compressed in the two chambers by using the prosthetic component as a pump. The pneumatic cylinder will then include an integral bleed.

The degree of airtightness necessary for correct functioning under high pressure is advantageously ensured, where the piston rod of the pneumatic cylinder crosses the wall of the upper chamber, by a double seal under oil pressure.

Thanks to all the preceding particularities, it will be understood that the invention consists of rendering pressure tight the pneumatic part of the prosthetic knee and that it permits modification at will of the basic pressure inside the pneumatic system, this being possible at any time during the activities of the patient.

The "pressure" parameter being connected to the coefficient of compressibility of the gas, the higher pressure at rest the more the gas tends to become incompressible, which renders the pneumatic system more reactive.

If the pressure at rest inside the pneumatic system is substantially equal to the atmospheric pressure, the prosthetic knee according to the invention has the characteristics of the knee already known in orthopaedics. On the other hand, if the pressure at rest inside the pneumatic system is above atmospheric pressure, the prosthetic knee according to the invention then has characteristics for damping pendular movement tending towards or having the action of the hydraulic knee, as a function of the level of pressure charged into the pneumatic system.

Further, the invention permits, if the patient so wishes, to set or adjust this level of pressure according to his wishes.

In other words, the invention permits the polyvalence: for normal walking the patient will preferably adopt a pressure substantially equal to atmospheric pressure, and if he wishes to engage in an activity obliging him to use more violent efforts in his lower limbs, the patient will then adopt a higher pressure, a pressure which he will then be able to set himself as a function of the intensity these efforts have to provide.

DESCRIPTION OF A PREFERRED EMBODIMENT OF THE INVENTION

Figure 1A:
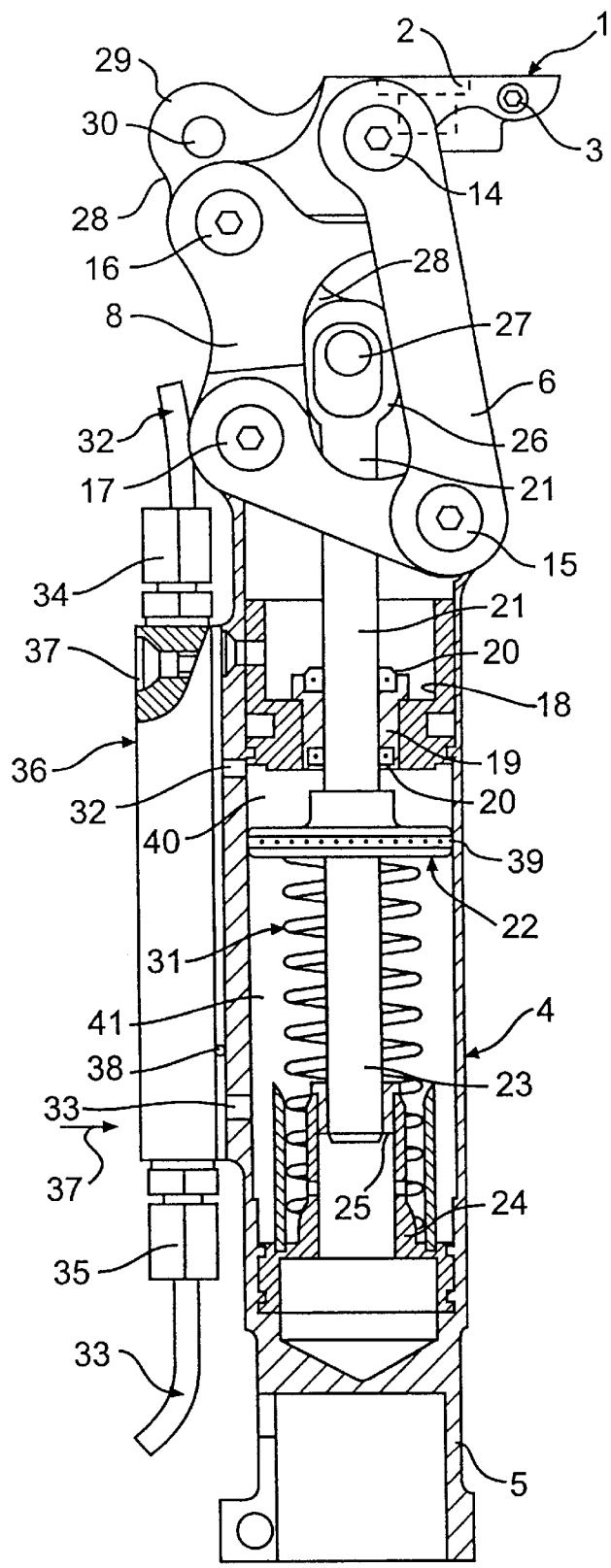
FIGS. 1A and 1B are respectively side and front views of the prosthetic component according to the invention shown in the position of complete extension.
Figure 1B:
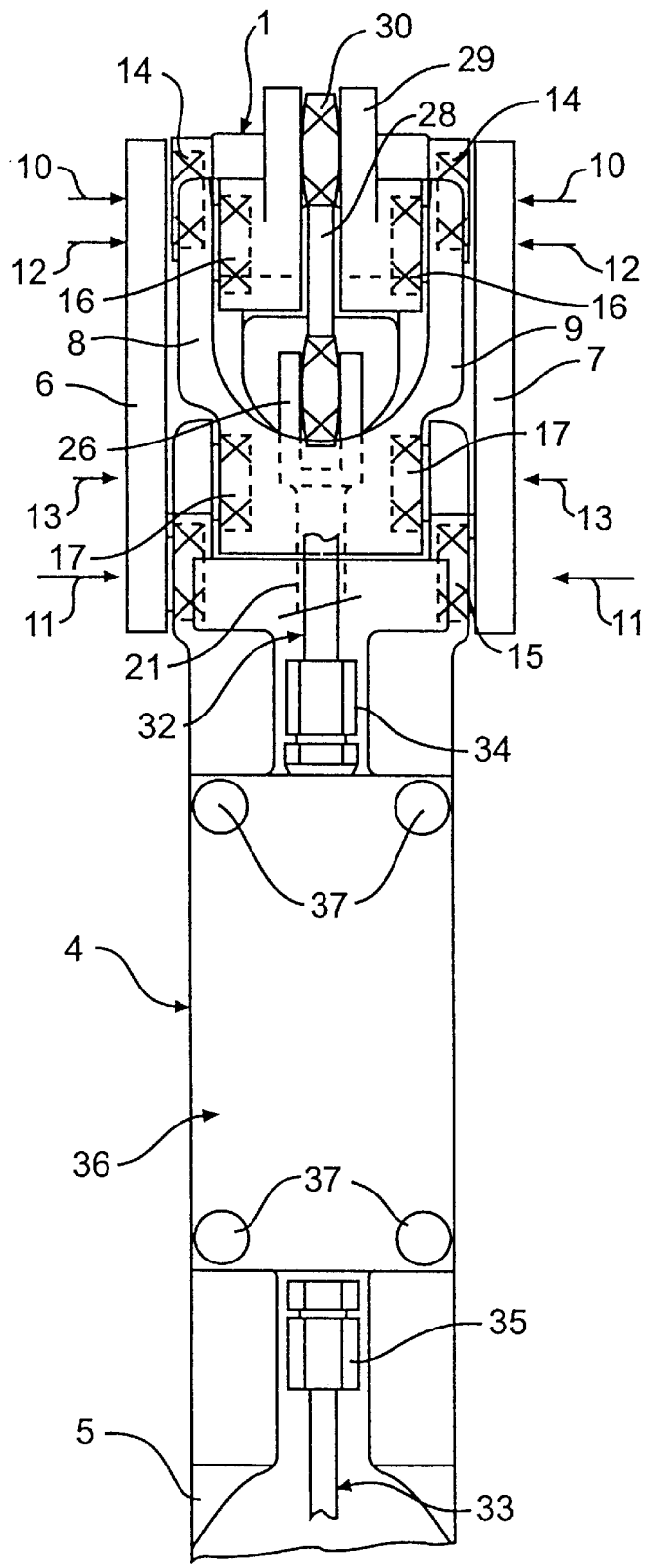

The references in FIGS. 1A and 1B will serve to describe the different characteristics of the invention.

The upper part of the prosthetic component is constituted by a platform 1 having a fixture hole 2 and threaded pins 3 for a socket (not shown) for the thigh stump of the amputee.

The lower part, forming the top end of the artificial leg, is essentially constituted by a tube 4. It is intended to receive in a socket 5 a tube extended by a ankle and foot (not shown).

The platform 1 and the tube 4 are connected to each other by an assembly of front 6, 7 and rear 8, 9 links forming a deformable prism. These, respectively front and rear, connection elements are pivoted about axes 10, 11, 12, 13 supported by bearings 14 and 15, arranged respectively at the front of the platform 1 and the upper part of the tube 4 and by bearings 16 and 17 arranged respectively at the rear of the platform and the upper part of the said tube. The rear links 8, 9 are unitary and form a single yoke. The bearings 14, 15, 16, 17 are ball, rolling element bearings.

Such an arrangement permits a movement of the upper part of the prosthesis with respect to its lower part, about a variable axis of rotation, analagous to the movement of the femur with respect to the tibia about the articulation of the human knee, between a position of complete extension (leg straight) and a position of complete flexure (leg bent). In the position of complete extension, the leg must be stiff and must not collapse under load. In the stages of balancing on the leg, whilst walking or running, the leg must be able to be propelled successively forwards and backwards.

In the prosthetic component according to the invention, the function of damping and propulsion is provided in a known manner by a pneumatic cylinder of which the body is constituted by the tube 4 of the tibial element. The tube 4 is closed at its lower end by the socket 5 serving also as the connection device for the prosthetic elements of the bottom of the leg. The upper part of the tube 4 is closed by a plug 18 incorporating a bearing 19 and a double seal 20 under oil pressure through which passes the upper rod 21 of the piston 22. The piston 22 has a lower rod 23 sliding in a support 24 provided with a bearing 25 and fixed on the socket 5 in a manner to ensure its appropriate guidance in the tube 4.

The upper rod 21 can be distinct from the lower rod 23, but advantageously the two rods 21 and 23 are integral and the single rod 21, 23 passes through the bearing 19 of the plug 18 and it also passes through the piston 22 this latter being however fixed on the rod 21, 23.

The upper rod 21 is provided with a yoke 26 inside which, around an axis of a bearing 27, is pivoted a link 28 making connection with the upper platform 1, which latter has a yoke 29 equipped with a bearing 30.

The compressed air in the lower chamber 41 of the pneumatic cylinder, that is to say delimited by the piston 22 and the socket 5, holds the platform 1 either in the position of complete extension shown in FIG. 1 (connection link 28 behind the pivot 14 of the front connection links 6, 7 on the platform 1), or in the position of complete flexure (connection link 28 in front of the said pivot 14). A compression spring 31 contributes to maintaining the stability of the assembly of the piston 22 and rods 21, 23 in each of these two positions of rest.

The compressed air in the upper chamber 40 of the cylinder, that is to say delimited by the piston 22 and the plug 18, allows damping of movement into abutment on flexure or extension.

The upper 40 and lower 41 chambers communicate by an air duct 32, 33 connected to the body of the cylinder by unions 34, 35 screwed to a hollow rectangular piece 36 held by four screws 37 onto the tube 4, which is locally flat and apertured through to the chambers. A flat elastomeric seal 38 ensures airtightness.

The piston 22 also has a peripheral O-ring 39, in order to isolate each of the two chambers 40, 41 from each other.

Figure 2:
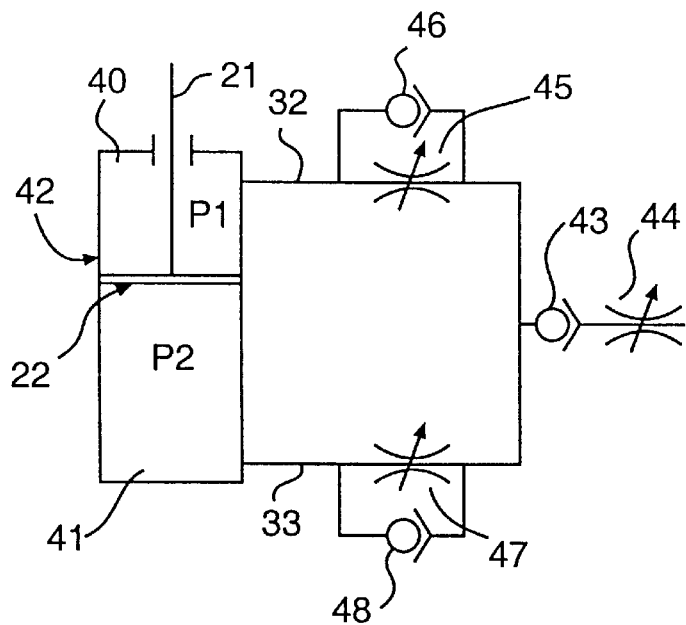
FIG. 2 is a block diagram of the pneumatics.

A perfect airtightness at all points is in fact an important condition for correct functioning of the present invention, which will now be explained with reference more particularly to FIG. 2.

In this Figure, are shown diagrammatically the upper and lower chambers 40, 41 delimited by the piston 22 in the pneumatic cylinder referred to in its entirety by the reference 42. These two chambers are connected to each other by the air duct 32, 33.

In the embodiments known in the state of the art, when the prosthesis is at rest (complete extension or flexure) and the piston is in its upper position, the pressure P1 in the upper chamber and the pressure P2 in the lower chamber are at the same pressure P0 equal to the atmospheric pressure Pa (1 bar).

Now supposing that the air duct 32, 33 interconnecting the chambers 40 and 41 is closed, if the piston 22 descends into the cylinder 42, the pressure P2 increases and the pressure P1 diminishes. A simple calculation, applying the law of compression of gasses at constant temperature, shows that, if the piston 22 is displaced by x, the differential pressure P between the two faces of the piston is proportional to P0 x.

If P0=Pa, upto angles of inclination of the order of 30° or 40° of the platform 1 relative to its horizontal rest position, an inclination which causes the piston 22 to descend, P is so low that the return force does not have the required value.

On the other hand, if P1=P2=P0=7 bar, for the same descent of the piston 22, a differential pressure P of the order of 6 bar is created. The return force is then strong and the propulsive force is considerable, even if the angle of inclination is low, of the order of a few degrees.

The invention, in one of its aspects, consists then in putting the air ducts 32, 33 in communication with the outside via a non-return valve 43. It is thus possible to compress ambient air into the chambers 40, 41 with an external inflation device.

The non-return valve 43 can be constituted simply by a valve of the "bicycle valve" type and it thus also has a obturator valve 44. The inflation device can be a simple bicycle pump of conventional type or having a pressure gauge.

The inflation to a more or less high pressure can allow the patient to adapt in a very simple manner, as a function of his needs, the orthopaedic characteristics of the prosthetic device for knee articulation according to the invention.

If the pressure at rest inside the pneumatic system is substantially equal to the atmospheric pressure, the knee has the characteristics of the knee already known in orthopaedics, and if the pressure at rest inside the pneumatic system is above atmospheric pressure, the knee then has characteristics for damping pendular movement tending towards or having the action of the hydraulic knee, as a function of the level of pressure charged into the pneumatic system, this level being able to be set by the patient according to his wishes.

The setting of the damping of the device is achieved separately for the movements of flexure and extension thanks to two adjustable valves provided in parallel with non-return valves.

The arm 32 of the air duct connecting the upper chamber 40 to the external valve 43, 44 has a first adjustable flexure valve 45, which sets the flow of air when the gas flows from the upper chamber 40 to the lower chamber 41. So that this valve has no effect on the flow of gas flowing in the opposite direction, a non-return valve 46 is arranged so that it allows free passage of gas in this case.

Conversely, the arm 33 of the air duct connecting the lower chamber 41 to the external valve 43, 44 has an adjustable extension valve 47, which sets the flow of air when the gas flows from the lower chamber 41 to the upper chamber 40.

A non-return valve 48 allows free flow of the air in the other direction.

The head-to-tail arrangement of the two valves 46, 48 thus allows total uncoupling of the actions of the first and second adjustable valves 45, 47.

Conventionally, the two valves 45, 47 can be controlled by adjustment screws arranged on the tibial element.

For greater comfort of use, and according to another feature of the invention, the controls of the valves 45, 47 can be moved to the socket or to the waist of the user of the prosthetic element.

Figure 3:
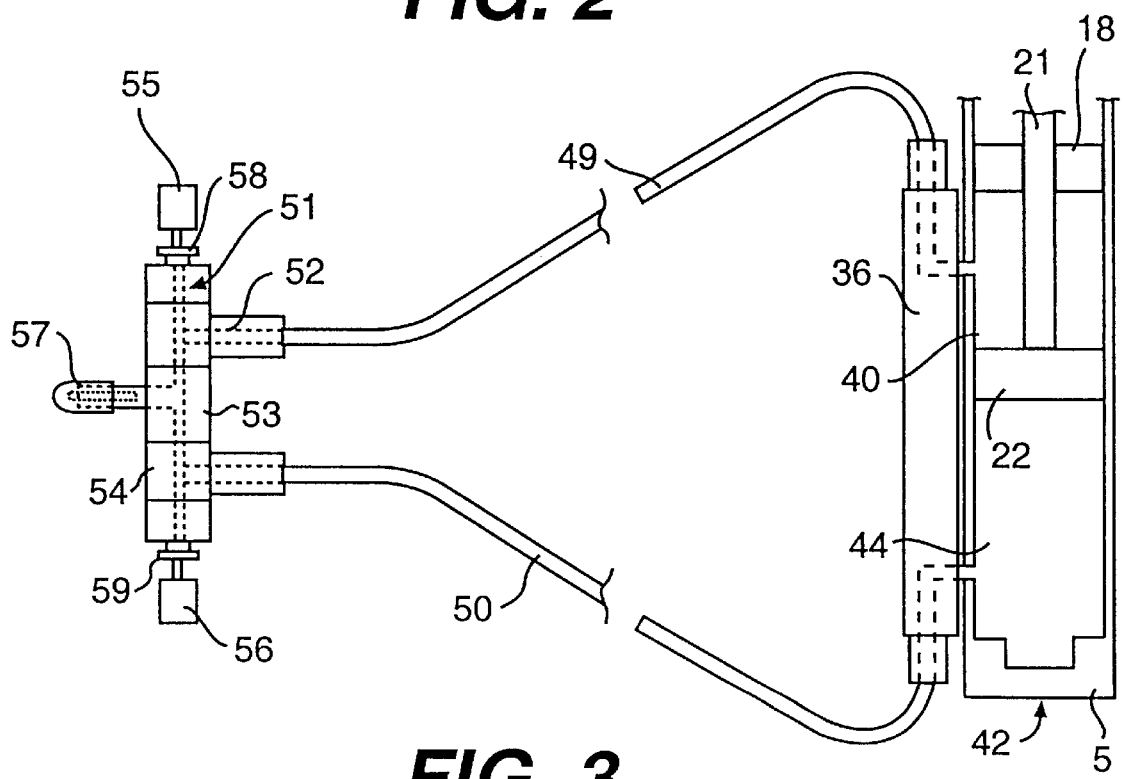
FIG. 3 is a diagrammatic view of the device for adjustment of the orthopaedic characteristics.

This characteristic will now be examined in more detail in connection with FIG. 3.

This figure shows that the two arms 32, 33 of the air duct are constituted by flexible tubes 49, 50 connecting the pneumatic cylinder 42 to the remote setting devices 51.

The assembly of three T connections, 52, 53, 54 allow connection of the two tubes 49, 50 of the air duct and of support of two screw needle valves 55, 56 with thumb wheels, each providing a valve and non-return valve, as well as the inflation valve 57.

The screw needle valves 55, 56 can be locked in their position corresponding to the desired setting by lock nuts 58, 59.

They can also comprise means for providing several pre-defined settings, such as notches or the like.

Alternatively, the screw needle valves can be replaced by multi-positioned obturators, providing smaller and larger passages for the flow of the gas. Preferably, these obturators will have a position for normal walking and at least one other position specific to the forces to be exerted, for instance for running or again for mountaineering, a sport where in certain circumstances it is necessary that the leg is as stiff as possible for an extended period of time.

According to another variant of the invention, the ambient air will be compressed by the prosthetic component itself, serving as a pump (auto-inflation). This pump will comprise an integral bleed.

In connection with FIGS. 4A to 4E, the different modes of operation of the prosthetic component according to this variant of the invention will be summarised by respective Tables 1 to 5.

Figure 4A:
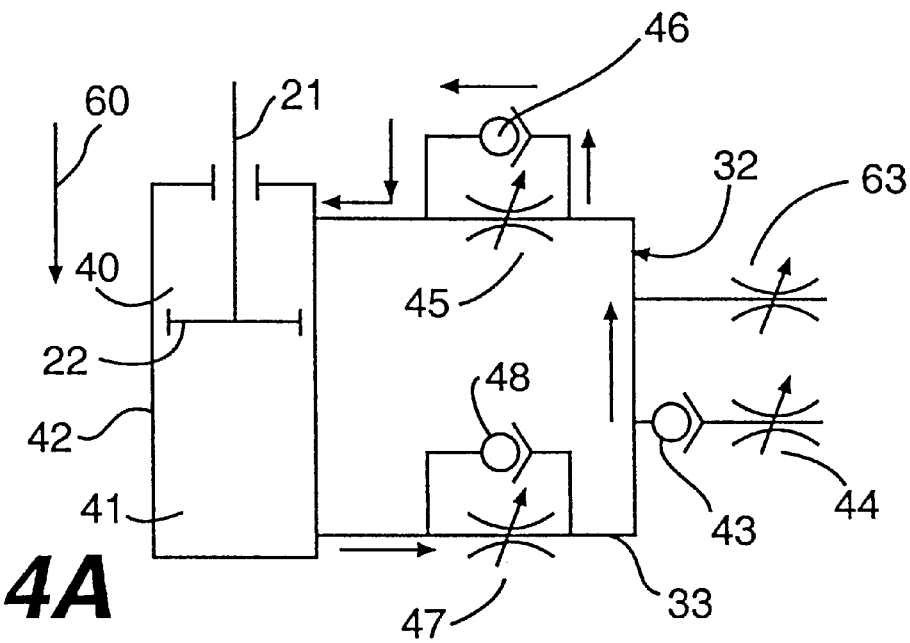
FIGS. 4A to 4E are pneumatic diagrams of a variant of the invention.

In FIG. 4A, referring to flexure, for which the movement of the piston is downwards as shown by the arrow 60, the flow of air being displaced from the lower chamber 41 to the upper chamber 40 is referred to by the arrows.

Figure 4B:
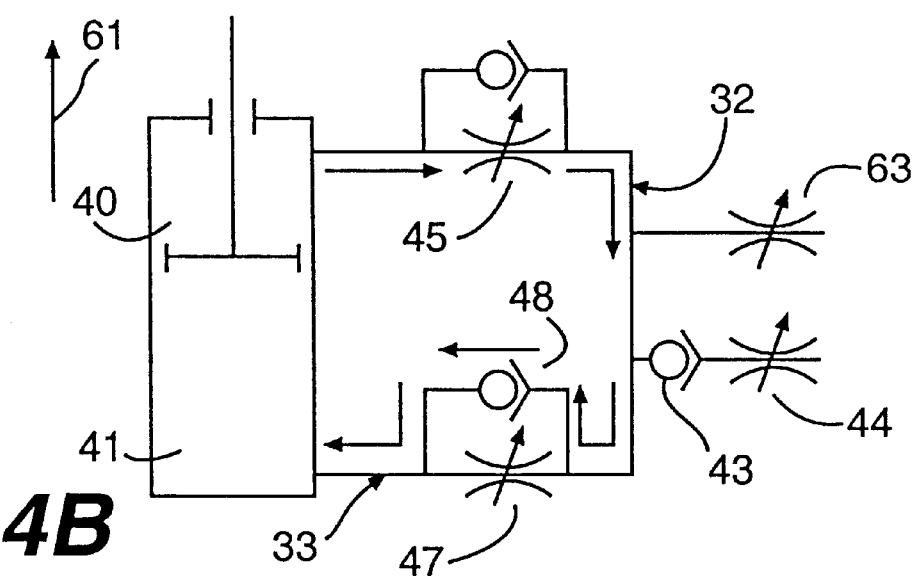

In FIG. 4B, referring to the extension, for which the movement of the piston is upwards as shown by the arrow 61, the flow of air being displaced from the upper chamber 40 to the lower chamber 41 is that referred to by the arrows.

Figure 4C:
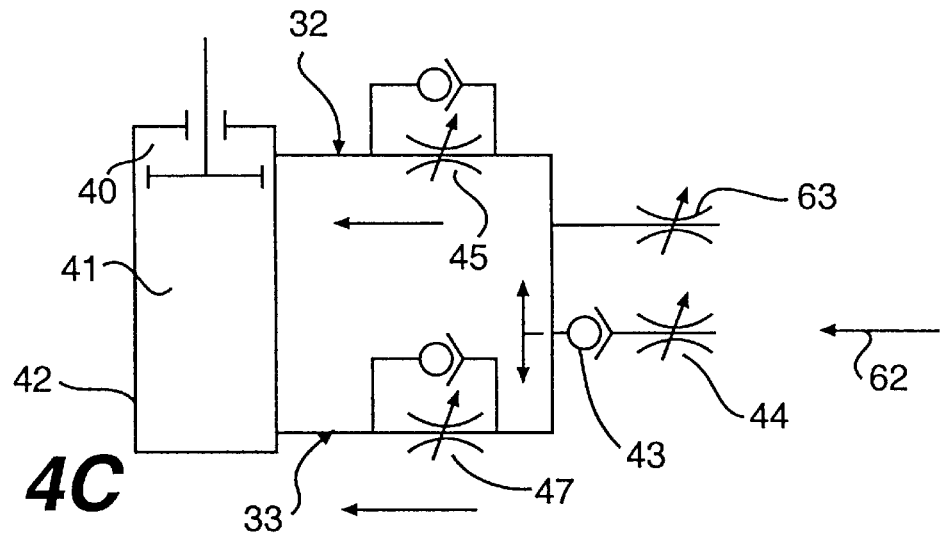

In FIG. 4C, referring to inflation at the same pressure of the two chambers 40 and 41 forming the pneumatic cylinder 42 with an inflation device 62, which can be manual or otherwise, whilst the knee is at rest, the inflow of charged air is referred to by the arrows.

Figure 4D:
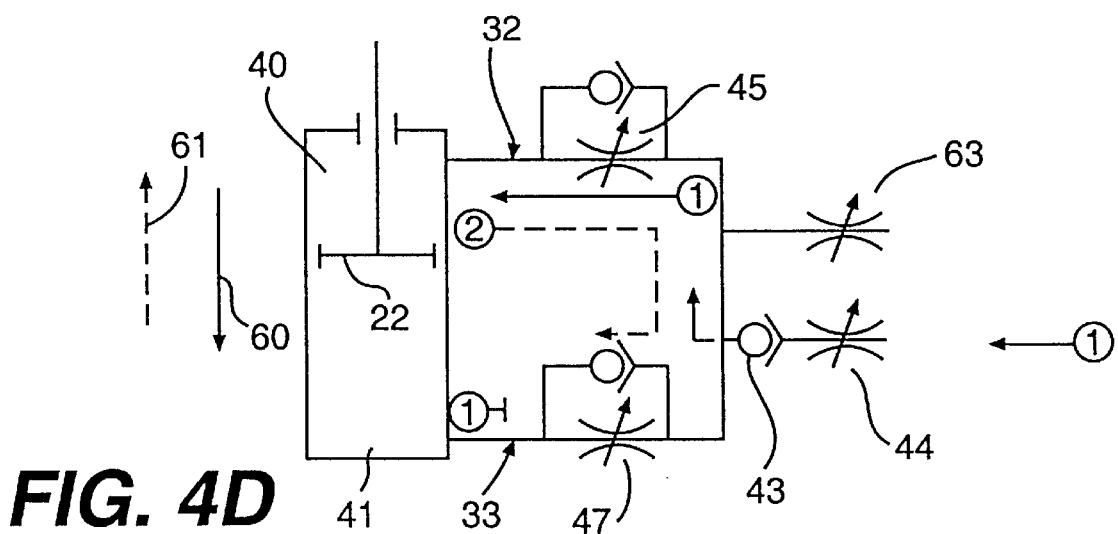

In FIG. 4D, referring to auto-inflation of the prosthetic component according to the invention, by alternative movements of flexure and extension of the leg, the flow of air is represented according to whether the simultaneous movement of the piston 22 is descent (flexure), in which case the ambient air is aspirated by the valve 44 to the upper chamber 40 and at a lower pressure than that in the lower chamber 41, or rising of the piston (extension), in which case the air present in the upper chamber is returned to the lower chamber, of which the internal pressure increases substantially relative to the initial situation, and so on.

Figure 4E:
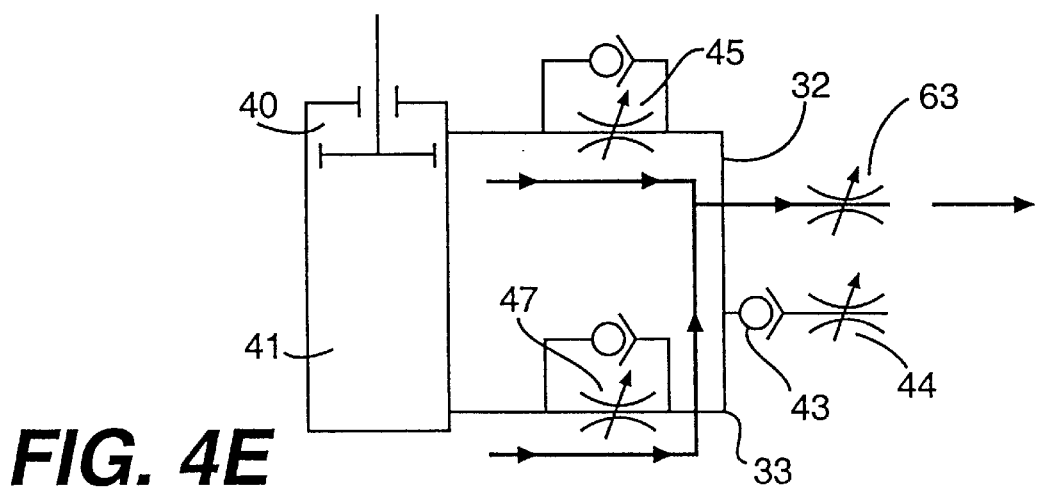

In FIG. 4E there is shown the emptying of the system with the valve 63 when open whilst the knee is in the rest position.

The Tables 1 to 5 record the positions of the valves 45, 47, 44 and 63 in relation to the operations shown in FIGS. 4A to 4E.

Naturally, the invention is not limited by the above technical description given by way of example; on the contrary, it includes all possible variants and embodiments.

| 1) Flexure: Valve States | | | | |
|---|---|---|---|---|
| | (45) | (47) | (44) | (63) |
| Maximum opening | | | | |
| Regulation | X | X | | |
| Closure | | | X | X |

| 2) Extension: Valve States | | | | |
|---|---|---|---|---|
| | (45) | (47) | (44) | (63) |
| Maximum opening | | | | |
| Regulation | X | X | | |
| Closure | | | X | X |

| 3) Pump Inflation: Valve States | | | | |
|---|---|---|---|---|
| | (45) | (47) | (44) | (63) |
| Maximum opening | X | X | X | |
| Regulation | | | | |
| Closure | | | | X |

| 4) Auto Inflation: Valve States | | | | |
|---|---|---|---|---|
| | (45) | (47) | (44) | (63) |
| Maximum opening | X | | X | |
| Regulation | | | | |
| Closure | | X | | X |

| 5) System Bleed: Valve States | | | | |
|---|---|---|---|---|
| | (45) | (47) | (44) | (63) |
| Maximum opening | X | X | | X |
| Regulation | | | | |
| Closure | | | X | |

We claim:

1. A prosthetic component with a pneumatic device for knee articulation having an upper part, configured to support a socket element for a stump of a thigh, a lower part configured to receive a member comprised of an ankle and foot, an assembly of pivoted links forming a deformable prism for providing a connection between said upper and lower parts and a pneumatic cylinder having an upper chamber, a lower chamber, a piston separating said chambers and an adjustable flow, air duct providing communication between said chambers for controlling the movement of said two parts between two stable positions of complete extension and flexure, about a variable axis of rotation defined by said connections, and having the function of damping the end of a stroke and of propulsion by compressed air; the improvement comprising that, in each of said stable positions, the pressure of air in said chambers is greater than 1 bar, a first non-return valve for inflation via which said air duct is in communication with the ambient air, wherein a first arm of said air duct connecting said upper chamber to said first non-return valve comprises a second non-return valve and a first adjustable valve in parallel therewith and a second arm of said air duct connecting said lower chamber to said first non-return valve comprises a third non-return valve and a second adjustable valve in parallel therewith.

2. A prosthetic component according to claim 1, wherein said first and second arms of said air duct are constituted by flexible tubes of sufficient length to permit control of said first and said second adjustable valves from said socket element or a wearer's waist.

3. A prosthetic component according to claim 2, including a control of said first and second adjustable valves having several pre-defined settings.

4. A prosthetic component according to claim 3, wherein said control has two pre-defined settings.

5. A prosthetic component according to claim 1, wherein said first and second adjustable valves are constituted by an obturator with several positions.

6. A prosthetic component according to claim 5, wherein said obturator has two positions.

7. A prosthetic component according to claim 1, in combination with an associated inflation apparatus for compressing the ambient air to obtain said pressure in said chambers.

8. A prosthetic component according to claim 1, wherein said adjustable valves and said non-return valves are part of a configuration for utilising said prosthetic component as a pump for compressing the ambient air into said chambers.

9. A prosthetic component according to claim 8, including an integral bleed in said pneumatic cylinder.

10. A prosthetic component according to claim 1, wherein said piston of said pneumatic cylinder has an upper part of an upper rod connected to it, which upper part passes through an upper wall of said upper chamber by means of a bearing provided with a double seal under pressure oil.

11. A prosthetic component according to claim 1, wherein said pressure of air is between 4 and 7 bar.

* * * * *